US010495657B2

(12) United States Patent
Malinowski

(10) Patent No.: US 10,495,657 B2
(45) Date of Patent: Dec. 3, 2019

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Michal Malinowski, Bietigheim-Bissingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/863,028

(22) Filed: Jan. 5, 2018

(65) Prior Publication Data

US 2018/0217174 A1    Aug. 2, 2018

(30) Foreign Application Priority Data

Jan. 31, 2017    (EP) .................................... 17153954

(51) Int. Cl.
*G01N 35/04* (2006.01)
*G01N 35/00* (2006.01)
*G01R 19/25* (2006.01)

(52) U.S. Cl.
CPC ....... *G01N 35/04* (2013.01); *G01N 35/00584* (2013.01); *G01R 19/2513* (2013.01); *G01N 2035/0475* (2013.01)

(58) Field of Classification Search
CPC ............. G01N 35/04; G01N 35/00584; G01N 2035/00445; G01N 2035/0475; G01N 2035/0477; G01R 19/2513; B65G 54/02
USPC ...................................................... 73/863.01
See application file for complete search history.

(56) References Cited

U.S. PATENT DOCUMENTS

| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |

(Continued)

FOREIGN PATENT DOCUMENTS

| CN | 201045617 Y | 4/2008 |
| CN | 102109530 A | 6/2011 |

(Continued)

*Primary Examiner* — Nathaniel T Woodward
(74) *Attorney, Agent, or Firm* — Roche Diagnostics Operations, Inc.

(57) ABSTRACT

A laboratory sample distribution system is presented. The system comprises carriers to carry sample containers. Each carrier comprises a magnetically active device. The system comprises a transport plane to support the carriers and electro-magnetic actuators stationary arranged below the transport plane. The actuators move the carriers on top of the transport plane by applying a magnetic force to the carriers. The system comprises a control device to control the movement of the carriers on top of the transport plane by driving the actuators such that the carriers move along corresponding transport paths simultaneously and independently from one another and a sensor to measure supply currents and/or supply voltages. The actuators are supplied with electrical energy based on the supply currents and/or the supply voltages. The system comprises a monitoring device coupled to the sensor. The monitoring device monitors the actuators temperature based on the measured supply currents and/or supply voltages.

9 Claims, 2 Drawing Sheets

(56) References Cited

U.S. PATENT DOCUMENTS

| | | |
|---|---|---|
| 4,395,164 A | 7/1983 | Beltrop et al. |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,457,368 A | 10/1995 | Jacobsen et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,148,666 A | 11/2000 | Roesicke |
| 6,151,535 A | 11/2000 | Ehlers |
| 6,184,596 B1 | 2/2001 | Ohzeki |
| 6,191,507 B1 * | 2/2001 | Peltier ................ B65G 54/02 310/12.02 |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 8,973,736 B2 | 3/2015 | Johns et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 9,567,167 B2 | 2/2017 | Sinz |
| 9,575,086 B2 | 2/2017 | Heise et al. |
| 9,593,970 B2 | 3/2017 | Sinz |
| 9,598,243 B2 | 3/2017 | Denninger et al. |
| 9,618,525 B2 | 4/2017 | Malinowski et al. |
| 9,658,241 B2 | 5/2017 | Riether et al. |
| 9,664,703 B2 | 5/2017 | Heise et al. |
| 9,772,342 B2 | 9/2017 | Riether |
| 9,791,468 B2 | 10/2017 | Riether et al. |
| 9,810,706 B2 | 11/2017 | Riether et al. |
| 10,126,317 B2 | 11/2018 | Heise et al. |
| 2002/0009391 A1 | 1/2002 | Marquiss et al. |
| 2002/0028158 A1 | 3/2002 | Wardlaw |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276782 A1 * | 10/2015 | Riether ............... G01N 35/1081 700/230 |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0077120 A1 | 3/2016 | Riether |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |

(56) References Cited

U.S. PATENT DOCUMENTS

| | | |
|---|---|---|
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0106821 A1 | 4/2018 | Vollenweider et al. |
| 2018/0128848 A1 | 5/2018 | Schneider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217176 A1 | 8/2018 | Sinz et al. |
| 2018/0224476 A1 | 8/2018 | Birrer et al. |
| 2018/0348244 A1 | 12/2018 | Ren |
| 2018/0348245 A1 | 12/2018 | Schneider et al. |
| 2019/0018027 A1 | 1/2019 | Hoehnel |
| 2019/0076845 A1 | 3/2019 | Huber et al. |
| 2019/0076846 A1 | 3/2019 | Durco et al. |
| 2019/0086433 A1 | 3/2019 | Hermann et al. |
| 2019/0094251 A1 | 3/2019 | Malinowski |
| 2019/0094252 A1 | 3/2019 | Waser et al. |
| 2019/0101468 A1 | 4/2019 | Haldar |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-26808 A | 2/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2010-271204 A | 12/2010 |
| JP | 2013-172009 A | 2/2013 |
| JP | 2013-190400 A | 9/2013 |
| SU | 685591 A1 | 9/1979 |
| WO | 1996036437 A1 | 11/1996 |
| WO | 2003042048 A3 | 5/2003 |
| WO | 2007024540 A1 | 3/2007 |
| WO | 2008133708 A1 | 11/2008 |
| WO | 2009002358 A1 | 12/2008 |
| WO | 2010042722 A1 | 4/2010 |
| WO | 2012170636 A1 | 7/2010 |
| WO | 2010087303 A1 | 8/2010 |
| WO | 2010129715 A1 | 11/2010 |
| WO | 2012142250 A1 | 10/2012 |
| WO | 2012158541 A1 | 11/2012 |
| WO | 2013152089 A1 | 10/2013 |
| WO | 2013169778 A1 | 11/2013 |
| WO | 2013177163 A1 | 11/2013 |
| WO | 2014059134 A1 | 4/2014 |
| WO | 2014071214 A1 | 5/2014 |
| WO | 2015/104263 A2 | 7/2015 |

\* cited by examiner

LABORATORY SAMPLE DISTRIBUTION SYSTEM AND LABORATORY AUTOMATION SYSTEM

CROSS-REFERENCE TO RELATED APPLICATIONS

This application is based on and claims priority to EP 17153954.7, filed Jan. 31, 2017, which is hereby incorporated by reference.

BACKGROUND

The present disclosure generally relates to a laboratory sample distribution system and a laboratory automation system.

Known laboratory sample distribution systems are typically used in laboratory automation systems in order to transport samples contained in sample containers between different laboratory stations.

A typical laboratory sample distribution system comprises a number of sample container carriers adapted to carry one or more sample containers, a transport plane adapted to support the sample container carriers, a number of electro-magnetic actuators adapted to move the sample container carriers on top of the transport plane by applying a magnetic force to the sample container carriers, and a control device configured to control the movement of the sample container carriers on top of the transport plane by driving the electro-magnetic actuators.

Therefore, there is a need for a laboratory sample distribution system and a laboratory automation system having an increased reliability of operation.

SUMMARY

According to the present disclosure, a laboratory sample distribution system is presented. The laboratory sample distribution system can comprise a number of sample container carriers configured to carry one or more sample containers. Each sample container carrier can comprise at least one magnetically active device. The laboratory sample distribution system can also comprise a transport plane configured to support the sample container carriers and a number of electro-magnetic actuators stationary arranged below the transport plane. The electro-magnetic actuators can be configured to move the sample container carriers on top of the transport plane by applying a magnetic force to the sample container carriers. The laboratory sample distribution system can also comprise a control device configured to control the movement of the sample container carriers on top of the transport plane by driving the electro-magnetic actuators such that the sample container carriers move along corresponding transport paths simultaneously and independently from one another and a sensor configured to measure supply currents (Id) and/or supply voltages (Udc). The electro-magnetic actuators can be supplied with electrical energy based on the supply currents (Id) and/or the supply voltages (Udc). The laboratory sample distribution system can also comprise a monitoring device functionally coupled to the sensor. The monitoring device can be configured to monitor temperatures of the electro-magnetic actuators based on the measured supply currents (Id) and/or measured supply voltages (Udc).

Accordingly, it is a feature of the embodiments of the present disclosure to provide a laboratory sample distribution system and a laboratory automation system having an increased reliability of operation. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
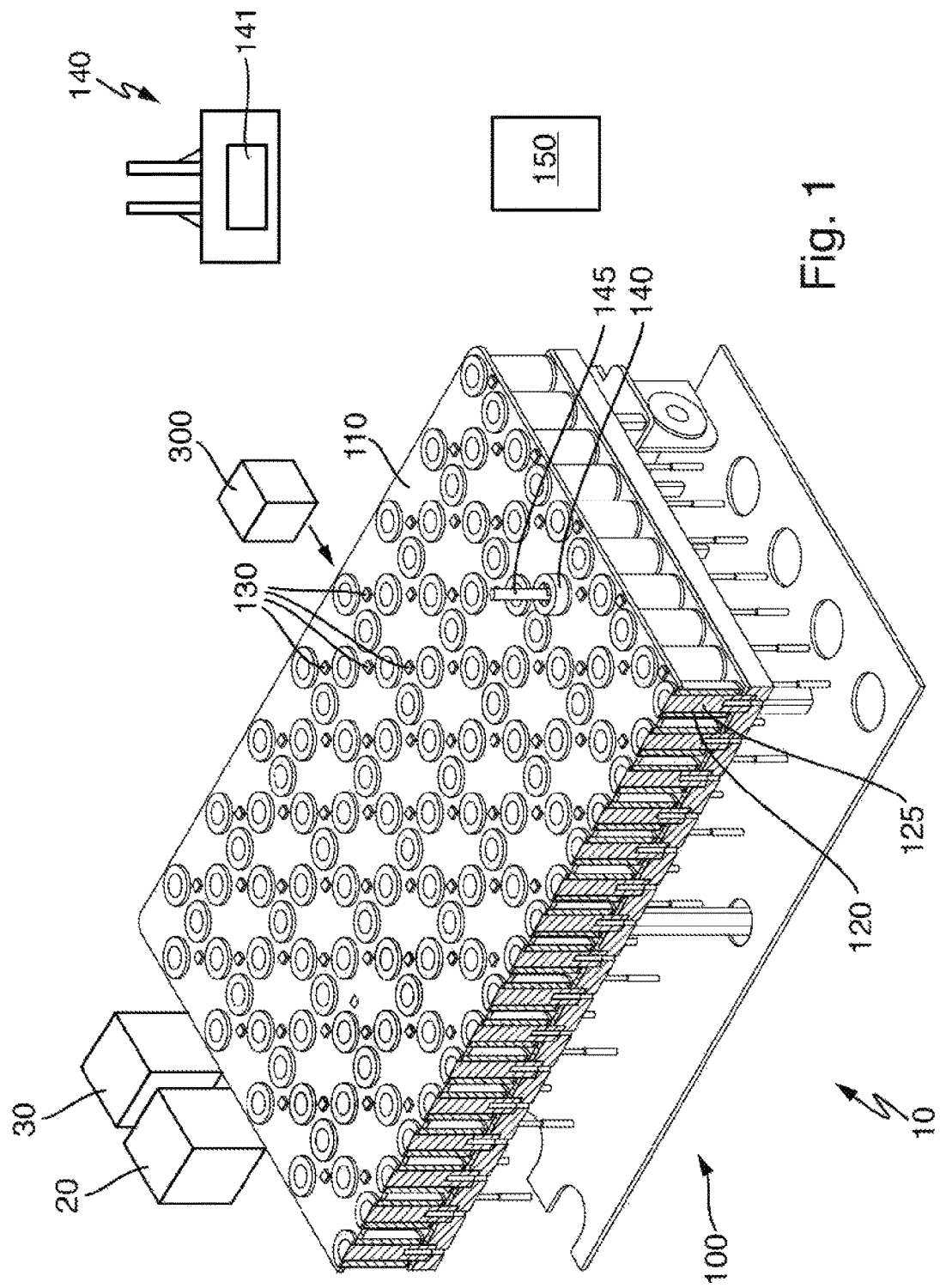
FIG. 1 illustrates a laboratory automation system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system is presented. The laboratory sample distribution system can comprise a number of sample container carriers. The number of sample container carriers may e.g. be a number in the range of 1 up to 1,000,000.

The sample container carriers can be configured to carry and/or hold and/or store one or more sample containers. The sample container can typically be designed as a tube made of glass or transparent plastic and typically can have an opening at an upper end. The laboratory sample container may be used to contain, store and transport the laboratory sample such as a blood sample, (blood) serum or plasma sample, a urine sample, separation gel, cruor (blood cells) or a chemical sample. The sample container may be rotationally symmetric.

Each sample container carrier can comprise at least one magnetically active device. The magnetically active device may e.g. be a permanent magnet or an electromagnet.

The laboratory sample distribution system can further comprise a transport plane configured to support or carry the sample container carriers. The transport plane may be a planar plane and the sample container carriers can be placed on top of the transport plane.

The laboratory sample distribution system can further comprise a number of electro-magnetic actuators. The number of electro-magnetic actuators may e.g. be a number in the range of 1 up to 1,000,000.

The electro-magnetic actuators can be stationary arranged below the transport plane, e.g. in rows and columns forming a grid. The electro-magnetic actuators may be embodied as coils having a ferromagnetic core. The coils may be configured to generate a magnetic field. The magnetic field generated by the electro-magnetic actuators may penetrate the transport plane. The magnetic field may interact with the magnetic field of the magnetically active devices of the sample container carriers. A magnetic force applied on the sample container carriers may be a result of this field interaction. Due to the magnetic force, the sample container carriers may slide and/or move over the transport plane.

Thus, the electro-magnetic actuators can be configured to move the sample container carriers on top of the transport plane by applying the magnetic force to the magnetically active devices of the sample container carriers.

The laboratory sample distribution system can further comprise a control device, e.g. in form of a personal computer (PC) or a microprocessor based control device. The control device can be configured to drive the electro-magnetic actuators. Each sample container carrier may move along a path in response to the driven electro-magnetic actuators. The path of the sample container carriers may be individual paths.

The laboratory sample distribution system can further comprise a, and in one embodiment, exactly one, sensor configured to measure a supply current and/or a supply voltage directly or indirectly supplied to a respective electro-magnetic actuator. The sensor may be embodied as a current sensor and/or a voltage sensor.

A respective electro-magnetic actuator can be supplied with electrical energy based on or dependent from the respective supply current and/or supply voltage. The respective supply current and/or supply voltage can depend on a temperature of the respective electro-magnetic actuator, typically the temperature of the coil of the respective electro-magnetic actuator. The supply currents and/or the supply voltages may be specific or identical for the respective electro-magnetic actuators.

The laboratory sample distribution system can further comprise a monitoring device functionally coupled to the sensor, e.g. configured to read the measured currents and/or voltages. The monitoring device can be configured to monitor the temperatures of the respective electro-magnetic actuators based on or in response to the respective measured currents/voltages. In one embodiment, the monitoring device can be configured to monitor the temperatures of the coils of the electro-magnetic actuators.

Typically, an electrical resistance of a respective electro-magnetic actuator or electro-magnetic actuator coil can depend on the temperature of the respective electro-magnetic actuator or electro-magnetic actuator coil. The respective (coil) resistance "$R_{Coil}$" may be calculated using the corresponding measured current and/or voltage.

If e.g. a voltage "U" applied to the respective electro-magnetic actuator is measured or known and the current I is measured, the respective coil resistance $R_{Coil}$ may e.g. be calculated using the formula:

$$R_{Coil}=U/I.$$

As known in the technical literature, the temperature dependency of the resistance $R_{Coil}$ of the coil can be denoted as follows:

$$R_{Coil}=R_{20°\ C.}*(1+\alpha_{20°\ C.}*(T_{Coil}-20°\ C.)),$$

wherein the term $R_{20°\ C.}$ denotes the resistance of the coil at 20° C., the term $\alpha_{20°\ C.}$ denotes the temperature coefficient of the coil resistance and the term $T_{Coil}$ denotes the temperature of the coil. Thus, the temperature $T_{Coil}$ may be calculated as $$T_{Coil}=(R_{Coil}-R_{20°\ C.})/(R_{20°\ C.}*\alpha_{20°\ C.})+20°\ C.$$

Thus, the temperature of the electro-magnetic actuators can be calculated using the measured currents and/or voltages.

According to an embodiment, the laboratory sample distribution system can comprise a single sensor configured to measure the supply currents and/or the supply voltages in a time multiplexed or sequential and repetitive manner. For example, the current and/or the supply voltage of a first electro-magnetic actuator may be measured by the sensor, then the current and/or the supply voltage of a second electro-magnetic actuator may be measured by the sensor, until the current and/or the supply voltage of all electro-magnetic actuators are measured by the sensor. Then, the process can start with the first electro-magnetic actuator again.

According to an embodiment, the laboratory sample distribution system can comprise a number (e.g. 1 to 1000) of conventional H-bridge circuits configured to generate drive signals, e.g. in form of drive voltages and/or drive currents, for the electro-magnetic actuators. The drive signals may depend on the supply current and/or depend on the supply voltage. H-bridge circuits are well known in the art, thus reference is made to the relevant technical literature.

According to an embodiment, the laboratory sample distribution system can comprise a voltage source configured to generate an output voltage as the supply voltages, i.e. the supply voltages can be identical to the output voltage. The H-bridge circuits can be supplied with the output voltage. The sensor can be configured to measure a current or currents supplied from the voltage source to the H-bridge circuits. Since the supplied currents are dependent on the temperature of the respective electro-magnetic actuator, the temperature of a respective electro-magnetic actuator may be determined based on the measured current.

According to an embodiment, the laboratory sample distribution system can comprise at least one fan configured to generate an airstream supplied to the electro-magnetic actuators, wherein the monitoring device can be configured to monitor the correct function of the at least one fan based on the measured currents and/or voltages. If the monitored temperatures do not match an expected temperature profile, a malfunction of the fan may be deducted.

According to an embodiment, the laboratory sample distribution system can comprise a memory configured to store the monitored temperature values to build a temperature history which may e.g. be used to check a deterioration of components.

According to an embodiment, the monitoring device can be configured to monitor a temperature of an electro-magnetic actuator only when the electro-magnetic actuator is not actively applying a magnetic force to a sample container carrier.

According to an embodiment, the electro-magnetic actuators can be formed as solenoids, wherein the solenoids can respectively comprise a ferromagnetic core and a coil surrounding the ferromagnetic core. The drive signals generated by the H-bridge circuits may be applied to the coils.

The laboratory automation system can comprise a number of laboratory stations and a laboratory sample distribution system as described above, wherein the laboratory sample distribution system can be configured to distribute the sample containers between the laboratory stations.

Pre-analytical stations may be adapted to perform any kind of pre-processing of samples, sample containers and/or sample container carriers.

Analytical stations may be adapted to use a sample or part of the sample and a reagent to generate a measuring signal, the measuring signal indicating if and in which concentration, if any, an analyte exists.

Post-analytical stations may be adapted to perform any kind of post-processing of the samples, sample containers and/or sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, a sample quality determining station, an add-on buffer station, a liquid level detection station, and a sealing/desealing station.

Referring initially to FIG. 1, FIG. 1 shows a laboratory automation system 10. The laboratory automation system 10 can comprise a first laboratory station 20, a second laboratory station 30 and a laboratory sample distribution system 100.

The laboratory sample distribution system 100 can comprise a transport plane 110. Under the transport plane 110, a plurality of electro-magnetic actuators 120, 125 in the form of solenoids can be arranged in rows and columns. Each electro-magnetic actuator can comprise a coil 120 and a corresponding ferromagnetic core 125, wherein the coil 120 can surround the corresponding ferromagnetic core 125.

A number of magnetic position sensors 130, embodied as Hall-sensors, can be distributed in rows and columns over the transport plane 110.

The laboratory sample distribution system 100 can further comprise a number of sample container carriers 140. A sample container carrier 140 can carry a respective sample container 145, embodied as laboratory sample tube. It can be noted that only a single laboratory sample container carrier 140 carrying a respective sample container 145 is shown in FIG. 1 for exemplary purposes. A typical sample distribution system 100 can comprise a plurality of sample container carriers 140.

Each sample container carrier 140 can comprise a magnetically active device 141 in the form of a permanent magnet. Thus, magnetic fields generated by the electro-magnetic actuators 120, 125 can drive a sample container carrier 140 over the transport plane 110.

Further, the magnetic field generated by the permanent magnet 141 of a sample container carrier 140 can be detected by the position sensors 130, so that a feedback regarding the position of a sample container carrier 140 can be obtained.

Both the electro-magnetic actuators 120, 125 and the position sensors 130 can be electrically connected to a control device 150. The control device 150 can drive the electro-magnetic actuators 120, 125 such that the sample container carriers 140 can move along corresponding transport paths. The control device 150 can also determine the position of each sample container carrier 140.

The laboratory stations 20, 30 can be arranged adjacent to the transport plane 110. It can be noted that the two laboratory stations 20, 30 are only shown for exemplary purposes in FIG. 1, and that a typical laboratory automation system 10 may comprise more than two laboratory stations 20, 30.

Figure 2:
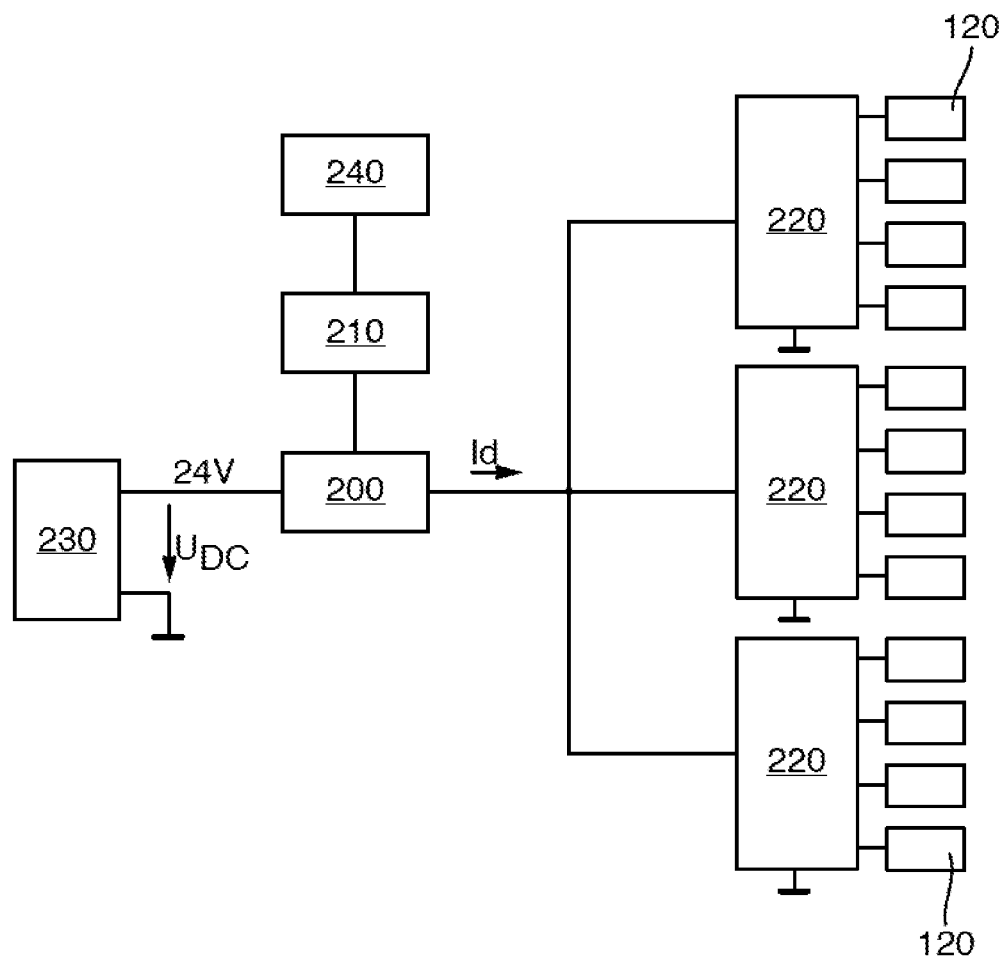
FIG. 2 illustrates a schematic block diagram of a driving circuit according to an embodiment of the present disclosure.

FIG. 2 shows a schematic block diagram of a driving circuit of the laboratory sample distribution system 100 used to drive the coils 120 of the electro-magnetic actuators.

The driving circuit can comprise a voltage source 230 generating an output voltage Udc having a known voltage level. The driving circuit can further comprise a number of H-bridge circuits 220, wherein the H-bridge circuits 220 can be supplied with the output voltage Udc. The depicted number of H-bridge circuits 220 is exemplary. Self-evidently, the driving circuit may comprise more than three H-bridge circuits 220 depending on the number of coils 120 needed in the laboratory sample distribution system 100. Each of the H-bridge circuits 220 can drive four coils 120. The H-bridge circuits 220 may be controlled by the control device 150.

The driving circuit can further comprise a sensor 200 configured to measure currents Id supplied from the voltage source 230 to the H-bridge circuits 220 in a time multiplexed manner. For each coil 120, a corresponding current Id can be measured when the corresponding H-bridge circuit 220 actively drives the coil 120.

The driving circuit further can comprise a monitoring device 210 functionally coupled to the sensor 200, wherein the monitoring device 210 can be configured to monitor a temperature of each of the electro-magnetic actuators (or monitor a temperature of the coil 120 of each of the electro-magnetic actuators) based on the measured supply currents Id and the known voltage Udc.

In order to monitor a temperature of an electro-magnetic actuator 120, 125, the monitoring device 210 can evaluate a resistance $R_{Coil}$ of the respective coil 120 based on the known voltage level of the output voltage Udc and the measured current Id. Based on the evaluated resistance $R_{Coil}$ the monitoring device 210 can evaluate the temperature $T_{Coil}$ of the coil 120 of the electro-magnetic actuator based on algorithms known in the art.

The driving circuit can further comprise a memory 240 configured to store the monitored temperature values.

Again referring to FIG. 1, the laboratory sample distribution system 100 can further comprise a fan 300 configured to generate an airstream supplied to the electro-magnetic actuators 120, 125. The monitoring device 210 can be configured to monitor the correct function of the fan 300 based on the measured currents Id.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a number of sample container carriers configured to carry one or more sample containers, each sample container carrier comprising at least one magnetically active device;
   a transport plane configured to support the sample container carriers;
   a number of electro-magnetic actuators stationarily arranged below the transport plane, the electro-magnetic actuators configured to move the sample container carriers on top of the transport plane by applying a magnetic force to the sample container carriers;
   a control device configured to control the movement of the sample container carriers on top of the transport plane by driving the electro-magnetic actuators such that the sample container carriers move along corresponding transport paths simultaneously and independently from one another;

a sensor configured to measure supply currents (Id) and/or supply voltages (Udc), wherein the electro-magnetic actuators are supplied with electrical energy based on the supply currents (Id) and/or the supply voltages (Udc); and a monitoring device functionally coupled to the sensor, wherein the monitoring device is configured to monitor temperatures of the electro-magnetic actuators based on the measured supply currents (Id) and/or measured supply voltages (Udc).

2. The laboratory sample distribution system according to claim 1, wherein the laboratory sample distribution system comprises exactly one sensor configured to measure the supply currents (Id) and/or the supply voltages (Udc) in a time multiplexed manner.

3. The laboratory sample distribution system according to claim 1, further comprises, a number of H-bridge circuits configured to generate drive signals for the electro-magnetic actuators.

4. The laboratory sample distribution system according to claim 3, further comprises a voltage source configured to generate an output voltage, wherein the supply voltages (Udc) are identical to the output voltage, wherein the H-bridge circuits are supplied with the output voltage, and wherein the sensor is configured to measure currents (Id) supplied from the voltage source to the H-bridge circuits.

5. The laboratory sample distribution system according to claim 1, further comprises, at least one fan configured to generate an airstream supplied to the electro-magnetic actuators, wherein the monitoring device is configured to monitor the correct function of the at least one fan based on the measured currents (Id) and/or voltages (Udc).

6. The laboratory sample distribution system according to claim 1, further comprises, a memory configured to store the monitored temperature values.

7. The laboratory sample distribution system according to claim 1, wherein the monitoring device is configured to monitor the temperature of an electro-magnetic actuator only when the electro-magnetic actuator is not actively applying a magnetic force to a sample container carrier.

8. The laboratory sample distribution system according to claim 1, wherein the electro-magnetic actuators are formed as solenoids and wherein the solenoids respectively comprise a ferromagnetic core and a coil surrounding the ferromagnetic core.

9. A laboratory automation system, the laboratory automation system comprising:

a number of laboratory stations; and a laboratory sample distribution system according to claim 1, wherein the laboratory sample distribution system is configured to distribute the sample containers between the laboratory stations.

* * * * *